(12) United States Patent
Parcher

(10) Patent No.: US 6,983,103 B1
(45) Date of Patent: Jan. 3, 2006

(54) COMBINED AUDIO LURE AND SCENT DISPENSER

(76) Inventor: Randy B. Parcher, 1156 Fenwick Rd., Fenwick, MI (US) 48834

( * ) Notice: Subject to any disclaimer, the term of this patent is extended or adjusted under 35 U.S.C. 154(b) by 431 days.

(21) Appl. No.: 10/323,253

(22) Filed: Dec. 18, 2002

Related U.S. Application Data

(60) Provisional application No. 60/342,980, filed on Dec. 19, 2001.

(51) Int. Cl.
*F24F 6/00* (2006.01)

(52) U.S. Cl. .......................... 392/390; 392/403; 222/3; 222/146

(58) Field of Classification Search ................ 392/386, 392/390, 344, 402, 403; 222/3, 146
See application file for complete search history.

(56) References Cited

U.S. PATENT DOCUMENTS

| | | | |
|---|---|---|---|
| 3,641,575 A | * | 2/1972 | Auer et al. ............ 340/825.61 |
| 5,429,271 A | * | 7/1995 | Porter ............................ 222/3 |
| 5,555,664 A | * | 9/1996 | Shockley .......................... 43/1 |
| 6,361,752 B1 | * | 3/2002 | Demarest et al. ........... 422/306 |
| 6,414,906 B1 | * | 7/2002 | Gaspari ...................... 367/139 |

* cited by examiner

*Primary Examiner*—Thor Campbell
(74) *Attorney, Agent, or Firm*—Young & Basile, P.C.

(57) ABSTRACT

The invention is a combined scent dispenser and audible lure for hunters and outdoorsmen. The scent-dispensing section of the invention is provided with an electrical heating element. Pre-recorded sounds stored within a memory in the invention may be played on command and transmitter by a speaker. Both the electrical heating element and the audible lure are provided with, in one embodiment, a radio receiver circuit and control circuit to selectively operate the heating elements and audible lure. A remote transmitter is provided to permit the remote operation of either or both of the heating element and audible lure.

14 Claims, 3 Drawing Sheets

COMBINED AUDIO LURE AND SCENT DISPENSER

RELATED APPLICATIONS

This application is related to, and claims the benefit of priority from, U.S. Provisional Patent Application Ser. No. 60/342,980, filed Dec. 19, 2001.

BACKGROUND OF THE INVENTION

The present invention pertains generally to portable devices for the dispensing of lures, specifically odor producing products combined with a device for producing the simulated sounds of wildlife.

Hunters routinely use scents for two distinct purposes. First, certain types of masking scents are desirable to cover the smell of human odor. Masking human odor is important to the success of the hunt in many cases. Alternatively, there are certain particular scents which act as lures to particular species of animals.

A wide range of devices have been developed for the distribution of these scents. U.S. Pat. No. 2,959,354, issued to Beck, discloses a portable deer lure in the form of a container for holding cotton fibers saturated with liquid scent. These types of devices can be improved by supplying a measure of heat to the scent, and as a result, a variety of devices have been developed which utilize a small battery in association with a heat-generating circuit to supply heat to the scent, thereby improving its dispersion. Such a device is disclosed in U.S. Pat. No. 4,937,431, issued to Jamison.

Also useful to hunters are sound-generating devices capable of producing various sounds which tend to lure desired species in response to a sound or call. While mechanical sound-producing devices have been used in the past, it is now well known to create, store and broadcast an electronic reproduction of sounds of various game animals and birds. These sounds, as digital data, can be conveniently stored in read-only memory devices, often in the form of integrated circuits, which are small, lightweight, and consume very little power.

For these reasons, many hunters are currently equipped with both scent-dispensing devices, as well as separate sonic lures. It is preferable, however, that both the scent-dispensing devices and the sonic lures be positioned at a location remote from the position of the hunter. Ideally, both the scent-dispensing device and the sonic lure should be placed in a target area which, while remote from the hunter, is also visible to the hunter, and within the field of fire and range of the hunter's weapon. The positioning of a scent dispenser in one location, and the operation of a sonic lure by the hunter on his person has not been shown to be particularly effective in attracting and temporarily detaining prey in the hunter's field of fire.

There is a need, therefore, for a combined scent-dispensing system and sonic lure which may be remotely operated by the hunter.

It is an object of this invention to provide a scent-dispensing element and sonic lure element for the purpose of both containment and dispensing of odor-producing compounds for hunting, combined with a remotely operable sonic lure capable of producing simulated wildlife sounds. It is still another object to provide a combined package containing both the sonic and scent lure elements which can be located some distance from the hunter's position, yet remotely operable to minimize the likelihood that the hunter will be detected by his prey.

SUMMARY OF THE INVENTION

The foregoing and other objectives are achieved in a combined scent-dispensing and sonic lure which is remotely operable. The device comprises a housing which encloses all of the essential elements of the completed assembly.

The housing is provided with an accessible compartment designed to contain are movable open cell foam element capable of being wetted with a liquid scent. One side of the same compartment is provided with a beating element. The compartment is also provided with one or more covers which are latchable into position to effectively contain the scent when the device is in storage or otherwise not in use.

The housing further contains a separate compartment for holding one or more batteries and an associated electronic circuit for operating the heating element. The electric circuit is designed to cycle the heating element on and off at regular intervals to prevent overheating of the heating element, to provide the appropriate level of heat to insure dispersion of the scent, and to conserve electrical power by regulating the duty cycle of the heating circuit.

Also provided within the housing is an electronic sonic lure. The sonic lure includes a circuit having a programmable read-only memory device which is pre-programmed with digital data representing the sound of a particular species of wildlife. It is possible to include more than one pre-recorded digital sound pattern; the calls of both a male and female deer, for example, might occupy successive or separate locations in a single memory device. The sonic lure is further provided with a speaker or other sound-generating element, as well as the associated electronic circuitry for retrieving the pre-recorded digital sounds from memory and causing those sounds to be played through the speaker or sound-generating device.

Because the most desirable location for the invention may be at a position remote from the hunter, both the scent-generating circuitry and sonic lure circuitry may be operable by remote control. In one embodiment of the invention, both the heater circuit and the sonic lure circuit are coupled to a radio receiver circuit which selectively activates and deactivates either or both of the heater element or sonic lure circuits. A small and portable remote control is provided with switches for activating an internal transmitter, which will transmit, over relatively long distances, the necessary signal to the receiver circuitry, thereby activating either or both of the heating elements and sonic lures.

To facilitate utilization of the invention, in some embodiments, the dispenser/sonic lure combination is provided with a mounting device to permit the dispenser to be hung from or otherwise affixed to a support, such as a tree branch or fence post.

DETAILED DESCRIPTION OF THE INVENTION

Figure 1:
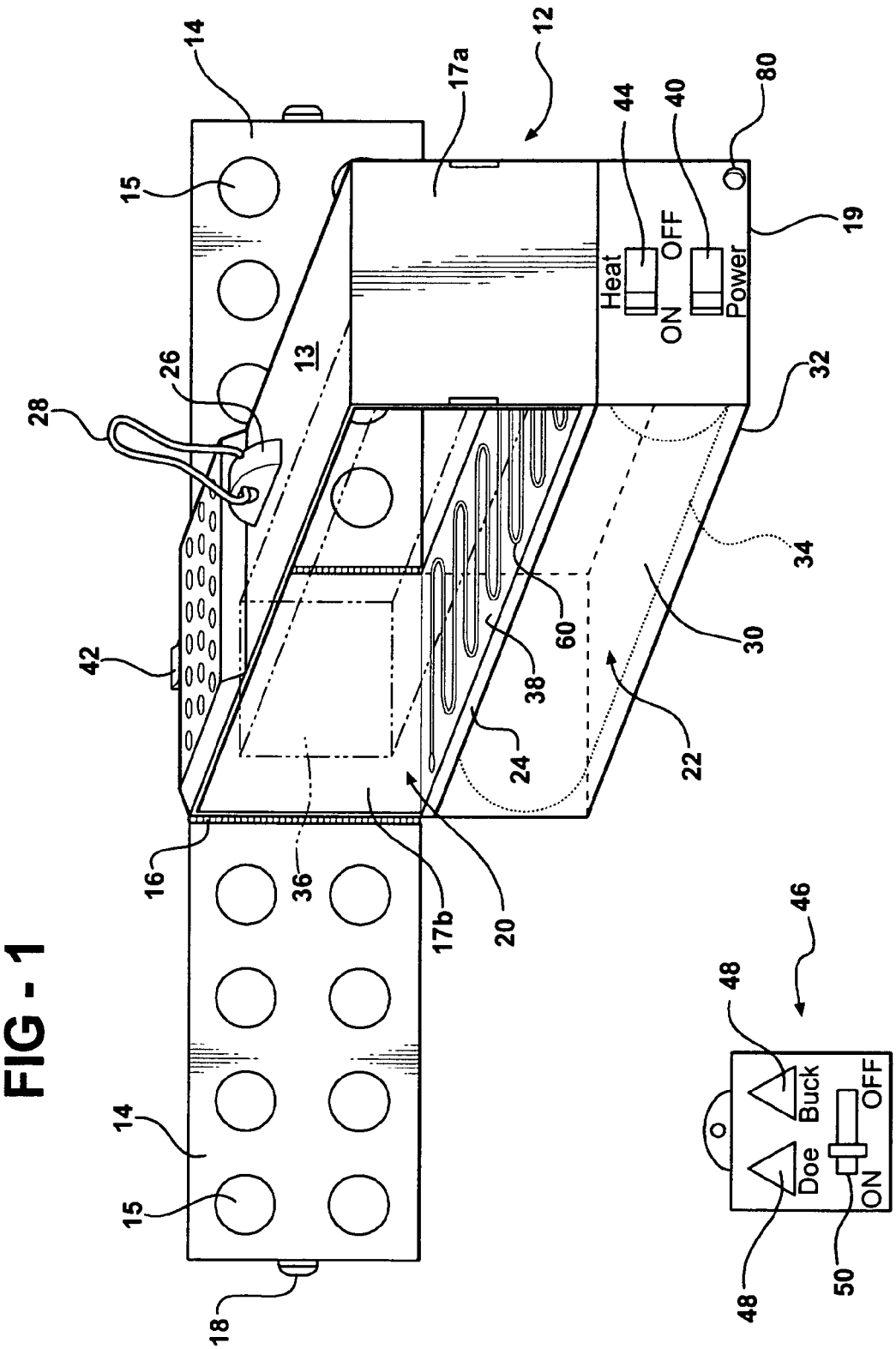
FIG. 1 is a perspective view of the sonic lure and its associated remote control.

Referring first to FIG. 1, it will be seen that the invention is a combined scent dispenser and sonic lure 10 consisting of a housing 12 provided with doors 14 mounted to pivoting hinges 16 which are provided with catches 18 permitting the doors 14 to be selectively opened and closed to expose or contain scent compartment 20. The housing is further provided with a top 13, sides 17a and 17b and bottom 19. Adjacent the scent compartment 20 is a battery compartment 22 provided with a battery compartment cover 32. In one embodiment, the housing 12 is provided with an attach point 26, suitable for securement of a lanyard 28 or similar attachment device. Battery compartment 30 is preferably provided with one or more batteries 34 which serve to provide electrical power to the circuitry to be herein described.

The doors 14 which cover scent compartment 20 may be selectively positioned in closed, fully or partially opened positions to regulate the amount of scent dispensed and to some degree, the direction of its dispersion. The doors may also be provided with openings 15. The scent compartment is provided with a heating element 24 powered by battery 34 through the electronic circuitry shown in FIG. 3, to be later discussed in detail.

Also provided with the invention is a remote transmitter 46 provided with sonic lure selection switches 48 and scent dispenser heating element on/off switch 50. The remote is designed to be small, self-contained and lightweight, and is provided with a transmitter circuit and power supply to be discussed in further detail herein. In one embodiment of the invention, the heating element 24 is integrated with the scent compartment bottom 38. The housing 12 is provided with a main power switch 40, a sonic lure power switch 42 and heater switch 44. The placement of the afore described three switches on the housing permits operation of the combined scent dispenser and sonic lure without the necessity to resort to the remote transmitter 46. A scent holder 36 is removably disposed within the scent compartment 20.

Figure 2:
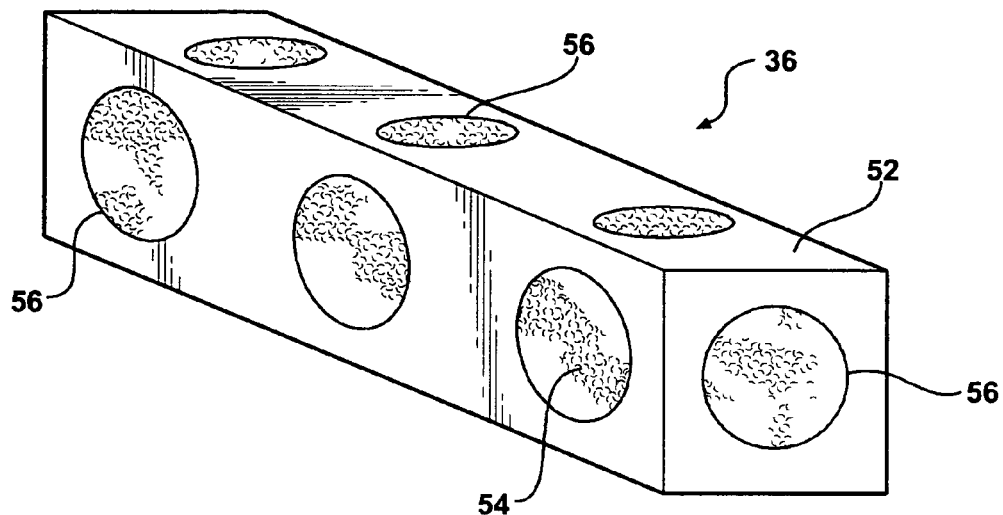
FIG. 2 is a perspective view of the scent holder enclosure and absorbent.

As shown in FIG. 2, the scent holder 36 consists of a scent holder enclosure 52 which may be formed of an easily formable and disposable material such as paper or cardboard. Likewise, a wide variety of plastics are suitable for the formation of the scent holder enclosure 52. Within the confines of scent holder enclosure 52 is a scent holder absorbent material 54 which may be open cell foam, cotton fibers, or material of like composition designed to absorb and hold liquid scents. The scent holder enclosure 52 is provided with opening 56 on one or more of its sides and perimeter to permit dispersion of the liquid scent carried by the scent holder absorbent material 54.

Figure 3:
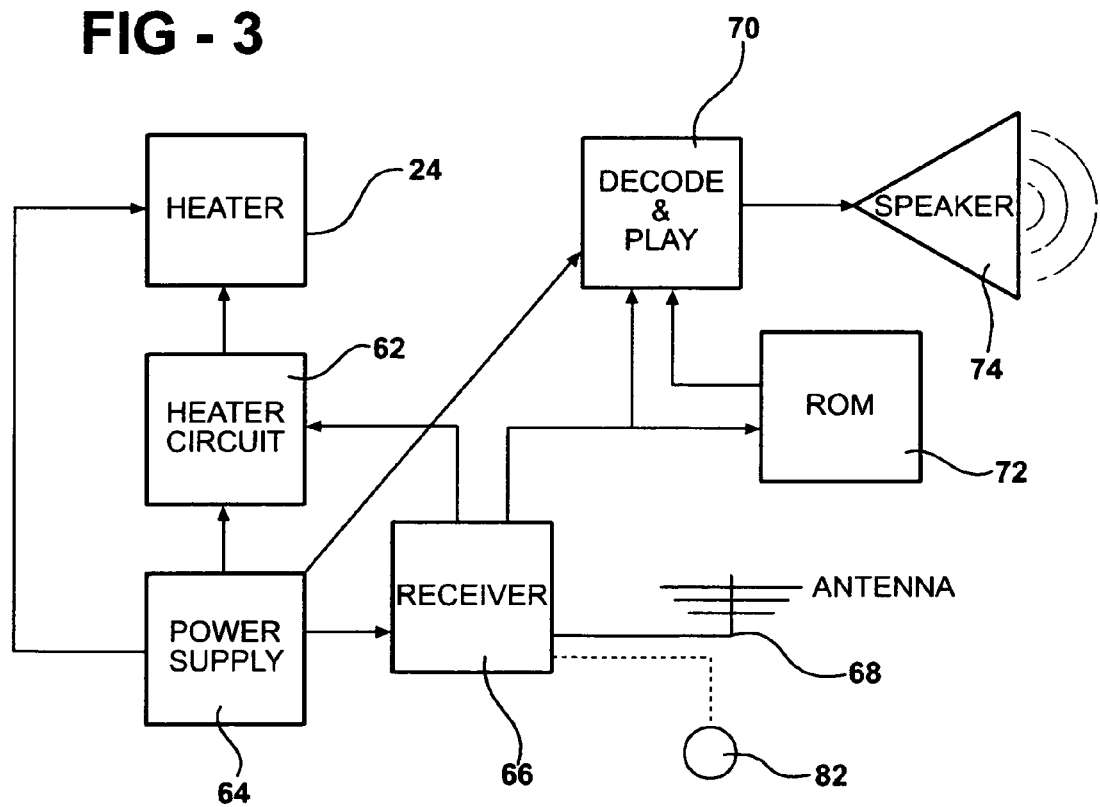
FIG. 3 is a block diagram of the electrical circuit of the invention.

Operation of the invention will be better understood by reference now to FIG. 1 and FIG. 3, which is a simplified schematic diagram showing the detailed operation of the scent dispensing and sonic lure aspects of the invention. In one embodiment, a heating element 24 is in the form of a resistance wire 60 which generates heat upon the application of an electrical current in a manner well known in the art. The resistance heating element may take the form of conventional Nichrome wire, or may be formed from resistive carbon material which can be painted or otherwise applied to the scent compartment bottom 38. To preserve battery power, the heater element 24 is connected to a cycling circuit 62 which may contain one or more control elements, such as a thermostat or timer to apply a selective amount of electrical current to the heater element 24, thereby cycling the power to the heater element 24 on and off and extending the life of the battery 34. Both the cycling circuit 62 and the heater element 24 receive power from a power supply circuit 64 which serves to establish and regulate the voltage from the battery 34 to that voltage desirable for effective operation of the control circuits and the heater element 24. The power supply circuit 64 further provides power to the radio receiver 66 and decoding and playing circuits 70 as further shown in FIG. 3. The receiver 66 is tuned to a discrete frequency identical to that utilized by the remote transmitter 46. A transmitted RF signal may be received by virtue of an antenna 68. In an alternate embodiment transmitter 46 may use infrared signals which are received by infrared sensor 82. Upon receipt of a "heat on" signal from the transmitter 46 or from the heat switch 44, the cycling circuit 62 is activated, causing the heater element 24 to function according to a predetermined cycle. The transmission of a "off" signal, or operation of the main power switch 40 to the "off" position serves to disable the cycle circuit 62 and turn the heater element 24 off.

In similar fashion, the receipt of a sonic lure signal from either the remote transmitter 46 or the lure switch 42 provides the instructions to enable the decoding and playing circuit 70 to extract the appropriate pre-recorded sounds from the ROM modules 72 and transmit said decoded data over the speaker 74. In one embodiment of the invention, the operation of the lure switch 42 serves to energize the decoding and playing circuit 70. The particular sounds to be played are selected by utilization of one of one or more lure switches 48 positioned on the remote 46. Although only two switches are depicted in FIG. 1, it will be readily apparent to those skilled in the art that more than two switches may be located on remote 48, depending on the number of prerecorded sounds to be selected. It will likewise be apparent to those skilled in the art that a single switch 48 may be used on the remote 46, and decoding circuitry provided in the receiver to select a particular prerecorded sound based on the number of times that the switch 48 is operated. For example, a single push of a switch 48 might select a first prerecorded sound, while two successive presses within a predetermined time frame of switch 48 will result in the playing of a second sound, for example. In the preferred embodiment, activation of the sonic lure circuit results in the playing of a single cycle of calls. Thereafter, the sonic lure is silenced until the remote switch 48 is operated again.

Figure 4:
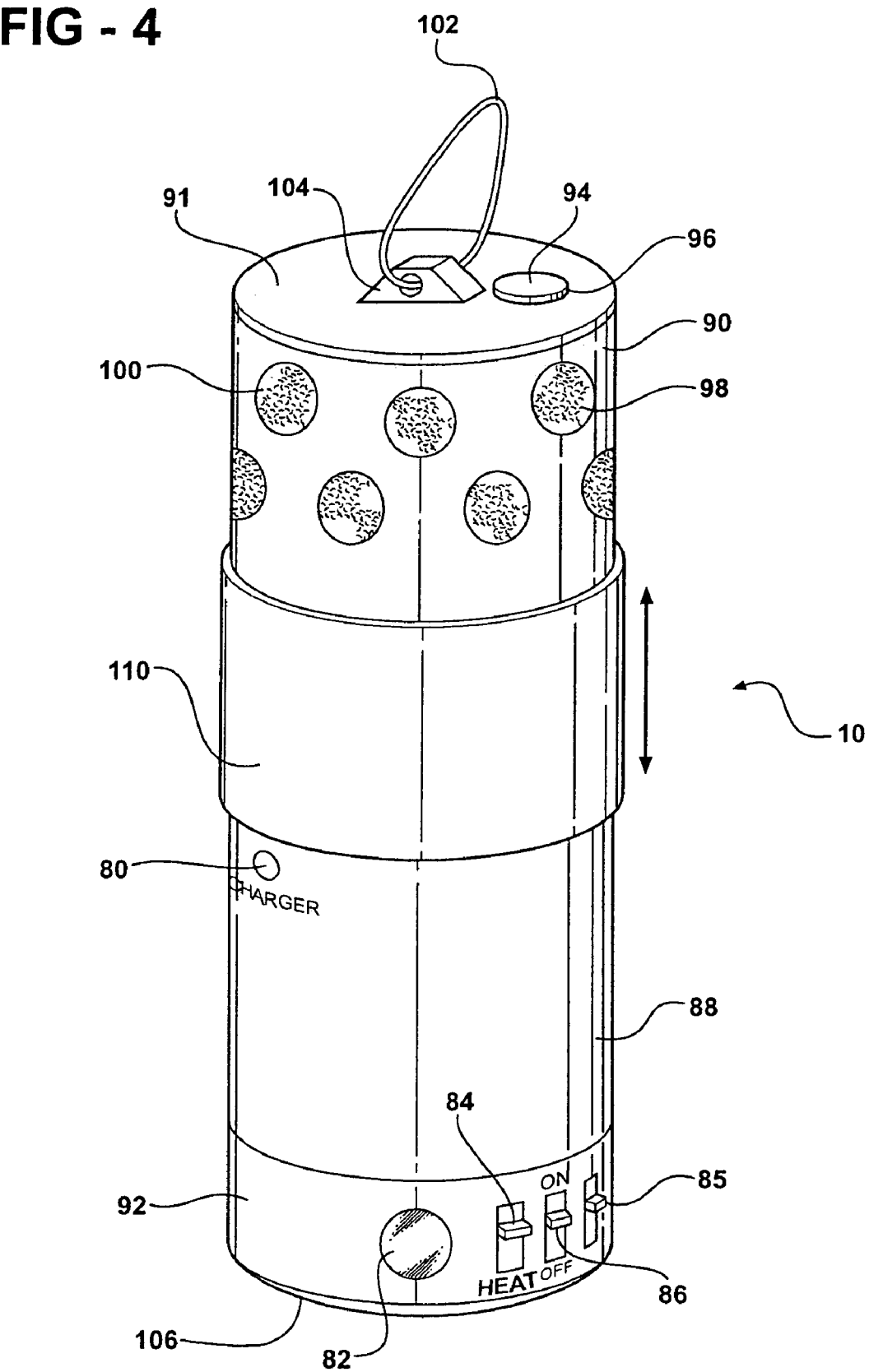
FIG. 4 is a perspective view of a second embodiment of the invention.

A second embodiment of my invention is depicted in FIG. 4. In this embodiment, the lure 10 is generally cylindrical in configuration, and is provided with a battery compartment 88 to which is threadably coupled a battery compartment cover 92 and a screw-on cap element 90. Absorbent 100 is contained within screw-on cap element 90 and a fill port 96, provided with a fill plug 94 which enables the user to open the top of screw-on cap 90 to introduce the liquid scent into the interior of space enclosed by screw-on cap 90, containing absorbent 100. In this embodiment, the lure is also provided with a lanyard 102 and a lanyard attaching point 104 to facilitate attachment of the lure to a hang point, such as a tree branch. The embodiment of the lure as shown in FIG. 4 further comprises a heater element (not shown) operated by a heater element switch 84. As in the first above-described embodiment, the heater element contained within the lure is operated by cycle circuitry 62 as shown in FIG. 3 whenever switch 84 is placed in the "on" position, to cycle the heater element between the "on" and "off" conditions, thereby generating heat to enhance disbursement of the scent from the absorbent material 100, while preserving the life of the batteries (not shown) contained within battery compartment 88. As is well known to those in the art, it is possible to provide batteries within compartment 88 which are rechargeable, such as nickel cadmium or lithium metal ion, in which case a charge receptacle 80 is provided in battery compartment 88 to facilitate connection of an external battery charging device (not shown). Power to the device is provided by batteries operating through an on-off switch 85 which energizes both the heater element switch 84 and the sonic lure switch 86. Switch 86 preferably features three settings, "off"; "remote", which allows the lure to generate sound when the remote transmitter 46 transmits a signal; and "auto" which allows the sonic lure to generate sound at a predetermined interval.

In the embodiment of the invention shown in FIG. 4, a radio signal-receiving antenna 68 (not shown) is incorporated in battery compartment cap 92. Alternatively, the signals transmitted from the remote 46 may be in the form of infrared light signals, which are sensed by infrared sensor 82, and provided to the receiver 66 as shown in FIG. 3 for decoding. Also, battery compartment cap 92 is provided with speaker 106 and sonic lure call power switch 86 which energizes the sonic lure decode and play circuitry of FIG. 3, selectively playing prerecorded sound through speaker 106 in a fashion identical to that described in the first embodiment.

With further reference to FIG. 4, the battery compartment 88 is surrounded by a slidable ring 110, positioned circumferentially around the exterior of battery compartment 88. A function fit between ring 110 and battery compartment 88 permits ring 110 to be selectively positioned over any or all of the screw-on cap element 90, thereby exposing none, some or all of the openings 98 in the screw-on cap 90. When ring 110 is pushed fully upward toward the top 91 of screw-on cap 90, the scent is effectively contained within screw-on cap 90. When the ring 110 is retracted to expose one or more openings 98 of cap 90, the scent contained within the absorbent 100 is thereby allowed to disseminate.

While the invention has been described in connection with what is presently considered to be the most practical and preferred embodiments the invention is not limited to those disclosed embodiments. To the contrary, the Applicant intends that this disclosure cover various modifications and equivalent arrangements included within the spirit and scope of the appended claims which scope is intended to be accorded the broadest interpretation so as to encompass all such modifications and equivalent structures as is permitted under the law.

What is claimed is:

1. A scent-dispensing device for distributing scent into the air comprising a compartment for containing a quantity of scented material, one or more selectively openable apertures in said compartment, a heating element adjacent to said compartment for selectively heating said scent, power means for applying electrical power to said heating element, cycling means for energizing and de-energizing said heating element at predetermined intervals, an audible lure, electronic control means for selectively controlling said heating element and said audible lure, and remote transmitter means for transmitting a signal to said electronic control means.

2. The invention of claim 1, wherein said signal is a radio frequency signal.

3. The invention of claim 1, wherein said signal is an infrared signal.

4. A scent-dispensing device for distributing scent into the air comprising a compartment for containing a quantity of scented material, one or more selectively openable apertures in said compartment, a heating element adjacent to said compartment for selectively heating said scent, power means for applying electrical power to said heating element, cycling means for energizing and de-energizing said heating element at a predetermined intervals, electronic memory means, predetermined data representative of an audible sound stored within said memory means, circuit means for converting said data to audible sound, an audible sound-producing device, and remote transmitter means for transmitting a signal to said scent-dispensing device.

5. The invention of claim 4, wherein said signal is a radio frequency signal.

6. The invention of claim 4, wherein said signal is an infrared signal.

7. A scent-dispensing device comprising a housing having a quantity of scented material disposed therein, an audible lure, a heating element disposed in the housing for heating said scented material, a cycling circuit operatively connected to said heating element for selectively energizing and de-energizing said element, and a power source operatively connected to said lure, heating element, and cycling circuit.

8. The invention of claim 7, wherein said housing further defines at least one aperture.

9. The invention of claim 8, further comprising an electronic control circuit coupled to said lure, heating element, cycling circuit, and power source.

10. The invention of claim 9 further comprising a receiver operatively connected to said control circuit and a remote transmitter capable of generating and broadcasting at least one signal to said receiver.

11. The invention of claim 10, wherein said at least one signal is a radio frequency signal.

12. The invention of claim 10, wherein said at least one signal is an infrared signal.

13. The invention of claim 10, further comprising said housing being substantially cylindrical and a substantially cylindrical collar slidably mounted to the exterior of said housing for adjustably covering said at least one aperture.

14. The invention of claim 10, further comprising said housing being substantially rectangular and a selectively openable covering for each of said at least one apertures.

* * * * *

UNITED STATES PATENT AND TRADEMARK OFFICE
CERTIFICATE OF CORRECTION

PATENT NO. : 6,983,103 B1
DATED : January 3, 2006
INVENTOR(S) : Parcher

It is certified that error appears in the above-identified patent and that said Letters Patent is hereby corrected as shown below:

<u>Title page,</u>
Item [57], ABSTRACT,
Line 5, delete "transmitter" and insert -- transmitted --;

<u>Column 2,</u>
Line 6, delete "are removable" and insert -- removable --;

<u>Column 4,</u>
Line 12, insert -- , -- between "embodiment" and "transmitter";
Line 13, delete "are received" and insert -- are served --;
Lines 17-18, delete "a 'off' signal" and insert -- an "off" signal --;
Line 50, delete "Absorbent 100" and insert -- Absorbent material 100 --;
Line 55, delete "absorbent 100" and insert -- absorbent material 100 --;

<u>Column 6,</u>
Line 16, delete "at a predetermined" and insert -- at predetermined --.

Signed and Sealed this

Fourth Day of April, 2006

JON W. DUDAS
*Director of the United States Patent and Trademark Office*